US00PP12030P2

(12) United States Plant Patent
Kumar et al.

(10) Patent No.: US PP12,030 P2
(45) Date of Patent: Aug. 7, 2001

(54) HYBRID MINT PLANT NAMED 'NEERKALKA'

(75) Inventors: Sushil Kumar; Nirmal Kumar Patra; Suman Preet Singh Khanuja; Ajit Kumar Shasany; Alok Kalra; Harikesh Bahadur Singh; Hemendra Pratap Singh; Ved Ram Singh; Nareshwar Mengi; Hasan Tanveer; Arif Ali Naqvi; Vijay Pal Singh; Kambod Singh, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/145,290

(22) Filed: Sep. 2, 1998

(30) Foreign Application Priority Data

Jun. 3, 1998 (IN) ..... 1509/98

(51) Int. Cl.[7] ..... A01H 5/00
(52) U.S. Cl. ..... Plt./259
(58) Field of Search ..... Plt./259

*Primary Examiner*—Bruce R. Campell
*Assistant Examiner*—Wendy C Baker
(74) *Attorney, Agent, or Firm*—Dorsey & Whitney LLP

(57) ABSTRACT

The present invention relates to the development of a new and distinct interspecific mint hybrid 'Neerkalka' developed by sexual crossing between improved Mother plant *Mentha arvensis* (cv Kalka) and pollen plant *Mentha spicata* (cv Neera), which hybrid is propagated vegetatively by suckers or stem cuttings and is stable for commerical cultivation.

1 Drawing Sheet

FIELD OF THE INVENTION

Figure 1:
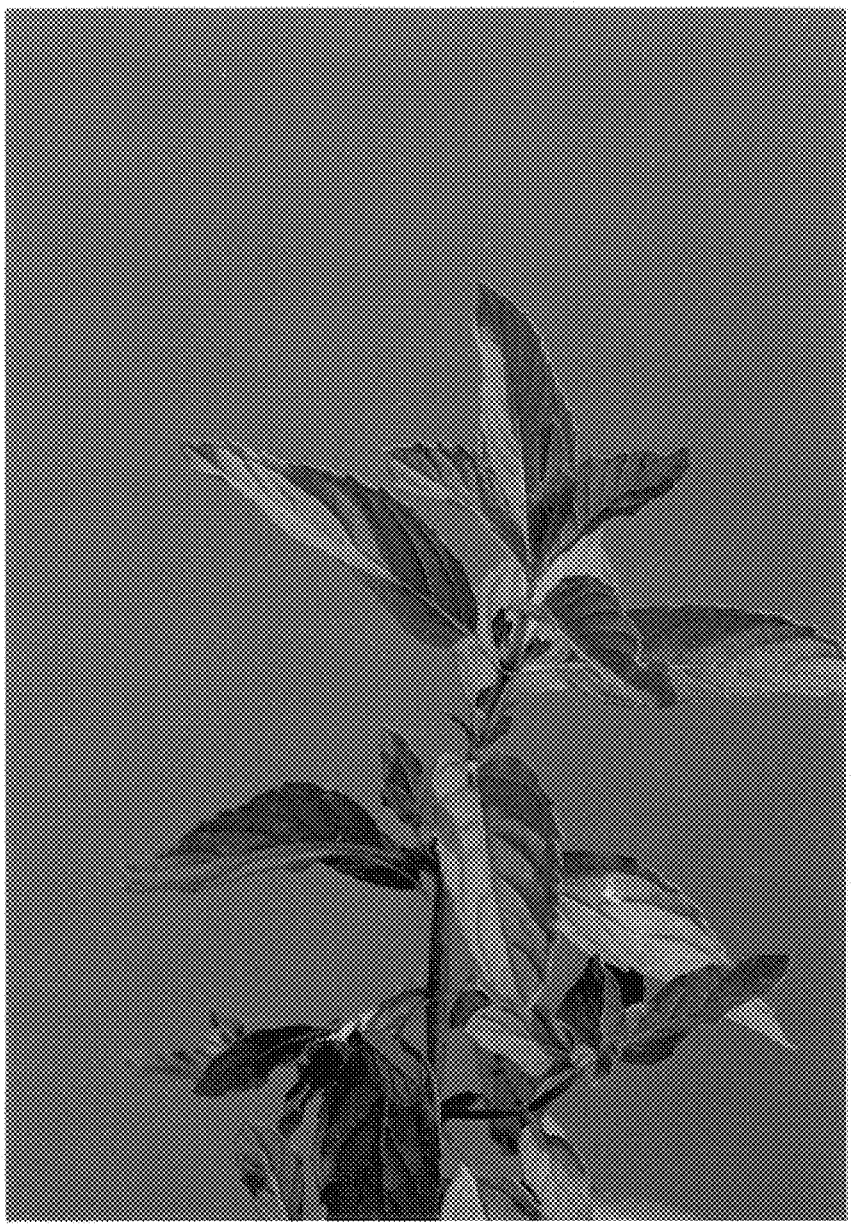

The present invention relates to a new and distinct interspecific hybrid mint plant namely 'Neerkala' which is developed by sexual crossing between improved *Mentha arvensis* (cv Kalka) and *Mentha spicata* (cv Neera). The hybrid is propagated vegetatively by suckers or stem cutting and is stable for commercial cultivation.

BACKGROUND OF THE INVENTION

Plants of the mint species are cultivated world wide for their specific mint aroma, which find uses in the culinary, antiseptic, confectionery and flavoring purposes. The distinct taste and aroma originating from the essential oils of different species in Mentha genus determine their specific use. The natural cross compatibility occurs between the species although manual emasculation and pollination is impeded due to extremely small size of the florets. *Mentha cardiaca* seems to have originated as a naturally occuring species believed to originate from the hybridization of *M. arvensis* and *M. spicata*. *Mentha arvensis* which is cultivated for mint oil has several widely adopted cultivars with superior agronomic traits. The variety 'Kalka' is one of the best cultivars grown widely by the farmers of India. Similarly, *Mentha spicata* cultivars released by Central Institute of Medicinal and Aromatic Plants (CIMAP), Lucknow, India, are widely adopted by the farmers for superior spearmint oil quality. One such cultivar is *Mentha spicata* 'Neera' or CIMAP/'Neera' which is distinctly different in its RAPD pattern from other available genotypes/varieties. It is known for its profuse flowering and seed setting habit. As such, the Applicants have combined the characters of these two mint species (*Mentha arvensis* and *Mentha spicata*) and developed a hybrid herb (*Mentha arvensis*×*M. spicata*) 'Neerkalka' which has high yield, desirable oil quality for various herbal uses like chewing gums, toothpaste etc. The selected hybrid clone retains the profuse growth habit of *Mentha arvensis* simultaneously expressing the "carvone type" mint oil characteristics of *Mentha spicata* and possesses the phenotype tending towards another naturally occuring species believed to originate from the hybridization of *M. arvensis* and *M. spicata*. The hybrid plant is more commercially acceptable due to its more favorable argonomic traits.

SUMMARY OF THE INVENTION

Accordingly, the present invention provides stable commercially cultivable hybrid mint plant 'Neerkalka' providing high herb yield, high oil yield and spearmint oil type with menthol tinge, which plant is developed by sexual crossing between improved *Mentha arvensis* (cv Kalka) and *Mentha spicata* (cv Neera).

DETAILED DESCRIPTION OF THE PRESENT INVENTION

The interspecific hybrid 'Neerkalka' has been developed by the Applicants by pollinating *Mentha arvensis* (cv Kalka) with pollen from *Mentha spicata* (cv Neera). The Applicants planted the parent plants *Mentha arvensis* (cv Kalka) and *Mentha spicata* (cv Neera) in alternate rows to favor crossing between them. The flowers of *Mentha arvensis* were dusted with the pollen collected from *Mentha spicata* flowers at regular intervals. The Applicants intention was to combine the better growth, menthol smell and disease resistance characters of Japanese mint with the carvone smell of spearmint to create a novel oil quality which can be more acceptable in pharmaceutical as well as confectionery industries. The mint species used as parents, were selected from the varieties already released by CIMAP and well accepted by the farmers and industries. The plants were grown at Pantnagar, India, in plots of 5 m×5 m. As the hybrid can reproduce vegetatively by vigorous suckers and the genotypic characters are firmly fixed, the genotype can be of immense importance as improved variety. Hence, the novelty of the invention is that the hybrid was developed from improved varieties of CIMAP which are well characterized for their genotypes. The hybrid plant thus produced has more biomass and oil yield (carvone based) than the parent *Mentha spicata* and the natural hybrid *Mentha cardiaca. The hybrid plant 'Neerkalka' is the distinct hybrid developed by the inventors through sexual crossing between female parent Mentha arvensis* (cv Kalka) and pollen donor *Mentha spicata* (cv Neera) whereas *Mentha cardiaca* (Syn. *Mentha gracilis* cv Cardiaca) is believed to have originated in nature by natural crossing between *Mentha arvensis* and *Mentha spicata*. In other words, the rationale behind the present invention was to combine the characters of two known mint species available with them, in a directed manner to yield a plant of high herb yield, high oil yield and spearmint oil type with menthol tinge.

Accordingly, the invention provides a novel hybrid plant *Mentha arvensis*×*M. spicata* 'Neerkalka' having the following combination of characters:

a. The said hybrid is a cross between female parent *Mentha arvensis* (cv Kalka) and pollen donor *Mentha spicata* (cv Neera),
b. The said hybrid is tolerant to leaf spot, rust and powdery mildew diseases,
c. The said hybrid contains both menthol and carvone in the essential oil,
d. The said hybrid produces more biomass and oil in comparison to *Mentha spicata* and *Mentha cardiaca* cultivars 'Neera' and 'MCAS 2',
e. The hybrid genotype has a unique RAPD profile, and
f. It has a pleasant smell of both carvone and menthol useful in medicinal and aromatic preparations.

In an embodiment, the present invention provides a hybrid yielding spearmint oil having the following ingredients: Limolene (6.8–23.2%), Menthol (0.66–2.45%), Carvone (64.0–76.1%) and other unidentified fractions in the essential oil totaling to 100%.

BRIEF DESCRIPTION OF THE ACCOMPANYING DRAWINGS

FIG. 1 is a photograph of a stem of the hybrid, 'Neerkalka' showing the size and color of the leaves.

BREEDING HISTORY

The new hybrid clone of the present invention is the mint plant developed in planned breeding programs conducted at Central Institute of Medicinal and Aromatic Plants (CIMAP), Lucknow, India and its field station Pantnagar, India. The early steps of development, such as crossing of parent lines, were conducted in CIMAP, Lucknow. The field trials were conducted at the field station at Pantagar, India.

The plant of the present invention has been asexually reproduced in the following manner. Generally, Mentha species are cultivated through suckers as normal mode of asexual commercial propagation. Suckers are the underground plant part which give rise to similar plantlets when planted in the field. The hybrid plant 'Neerkalka' produces enough suckers for asexual propagation. The stems of the plants were planted in the month of October in the field at CIMAP. The plants were established which produced underground suckers. These suckers were then planted in the main field in the month of January for trial.

The breeding method involved is of cross pollination of *Mentha arvensis* (cv Kalka) florets with *Mentha spicata* (cv Neera) pollen and the seeds thus obtained, were collected upon maturation. Out of a total of 260 seedlings raised from the hybrid seeds borne on the *Mentha arvensis* (cv Kalka), a single distinct plant nearing *Mentha cardiaca* phenotype including oil aroma was observed and subsequently selected. This selected plant which was propagated and multiplied vegetatively many times later, is the hybrid clone of the present invention, designated as 'Neerkalka' and referred as "hybrid" hereafter.

Since the florets of *Mentha arvensis* and *Mentha spicata* are very small in size, the manual emasculation and pollination are extremely difficult to achieve. To overcome this problem of controlled pollination, the approach of developing hybrid seeds was modified towards increasing the incidence of natural crossing between restricted parents only. For this purpose, the selected parents *Mentha arvensis* (cv Kalka) and *Mentha spicata* (cv Neera) were raised in alternate rows (2:1::Kalka:Neera) in the field from the genetically pure suckers (maintained in the breeder's plot in isolation). The plants raised in this way were grown to flowering. Natural crossing between these parents was allowed to occur but simultaneously the florets of *Mentha arvensis* were repeatedly dusted with *Mentha spicata* pollen collected manually. Seeds were collected from *Mentha arvensis* (Kalka) and bulked. Similarly, seeds from *Mentha spicata* (Neera) florets were collected. The bulked seeds were grown separately in flat earthen pots during winter. A total of 260 seedlings could be raised from the seeds collected from the florets of *Mentha arvensis*, whereas about 290 seedlings were obtained from *Mentha spicata*, which were raised successfully in individual pots. The seedling from *Mentha spicata* were almost alike in morphology as compared to the parental phenotype (Neera) and possessed similar carvone rich smell. All the seedlings from *Mentha arvensis* except one, resembled the morphology of *Mentha arvensis* (cv Kalka) and had menthol aroma. There was an exeptional single seedling resembling the cv Kalka growth habit with a carvone rich aroma supplemented with a menthol tinge, and thus having a pleasant novel combination in the essential oil. The distinct plant showed morphology approaching towards another species *Mentha cardiaca* but for growth properties, leaf size and herbage yield, it resembled *Mentha arvensis* (cv Kalka). The size and colour of the leaves in the hybrid are similar to *Mentha arvensis* (cv Kalka) whereas, the shape resembles the pollen parent *Mentha spicata* (cv Neera) (Photograph #1). There are 2 leaves at each mode, 4 at the apex, and the leaves are arranged in opposite decussate phyllotaxy. The aroma of the oil was predominantly like that of the pollen parent while the menthol tinge it possessed was inherited from the female parent; thus the plant with recombined character was named "Neerkalka". The two parental species, the hybrid and *Mentha cardiaca* were grown (planting date $18^{th}$ Jan., 1996) from pure suckers side by side in different plots and were compared among each other for the morphological characters. The plants species were grown at 150:30:30 ($N_2$:$P_2O_5K_2O$) urea, SSP, MOP fertilizer dose and harvested 110 days after planting to compare the yield attributes. The comparison of some of the characters are presented in Table 1. The color codes are according to The R.H.S. Colour Chart published by The Roal Horticultural Society, 80 Vincent Square, London SW1P 2PE, 1995.

EVIDENCE OF UNIFORMITY AND STABILITY

The genotype Neerkalka has remained stable and uniform for its morphological characters and showed consistency in performance for various quality attributes during its evaluation and vegetative multiplication till date.

TABLE 1

Characteristics of cv Neera, cv Kalka, cv MCAS2 and the newly developed hybrid clone Neerkalka of Mentha.

| Traits | Hybrid (Neerkalka) | *M. spicata* (Neera) | M. arvensis (Kalka) | M. cardiaca (MCAS 2) |
|---|---|---|---|---|
| 1. Plant height (cm) | 56.8 ± 2.13 | 52.4 ± 2.10 | 97.0 ± 2.16 | 48.6 ± 2.20 |
| 2. Leaf length (cm) | 7.42 ± 0.40 | 2.34 ± 0.16 | 9.90 ± 0.37 | 6.31 ± 0.32 |
| 3. Leaf width (cm) | 2.66 ± 0.18 | 0.18 ± 0.14 | 2.66 ± 0.10 | 1.12 ± 0.10 |
| 4. Leaf colour | green (137A) | green (137B) | green (137C) | green (137D) |
| 5. Leaf shape | green (137A) | green (137B) | green (137C) | green (137D) |
| 6. Hairiness | hairs on the veins, glabrous | hairs on the veins, glabrous | hairs on the veins, glabrous | hairs on the veins, glabrous |
| 7. Leaf margin | finely sharp serration | normal serration | normal serration | finely sharp serration |
| 8. Stem colour | green (144C) with purple pigments at the base (186C) | green (144C) with purple pigments at the base (186D) | green (144D) with purple pigments at the base (186C) | green (144C) with purple pigments at the base (186C) |
| 9. Influorescence | racemose of axillary verticicil-lasters | idefinite racemose | racemose of axillary verticicil-lasters | racemose of axillary verticicil-lasters |
| 10. Flower colour | whitish purple (69D) | whitish purple (69D) | whitish purple (69D) | whitish purple (69D) with purple tinge (73B) |
| 11. Single plant weight (g) | 184.4 ± 2.11 | 73.4 ± 3.27 | 208.0 ± 4.77 | 173.4 ± 3.05 |
| 12. Leaf: Stem | 0.61 ± 0.03 | 0.54 ± 0.01 | 0.90 ± 0.01 | 0.58 ± 0.02 |
| 13. Herbage yield (Quintal/hectare) | 128 | 80 | 165 | 94 |
| 14. Oil content (%) | 0.80 | 0.60 | 0.80 | 0.64 |
| 15. Oil yield (kg/hectare) | 102.4 | 48.0 | 132.0 | 60.2 |
| 16. Oil aroma | carvone based with menthol tinge | carvone based | menthol based | carvone based |
| 17. Growth habit | semi prostate | prostate | erect | erect |

The hybrid is resistant to leaf spot, rust and powdery mildew, when planted in the infected field. Only 0–4 plants in the field of 2000 were observed to developed these diseases in separate trials. These resistant characters are apparently inherited from the parent *M. arvensis* (cv Kalka). Till date the hybrid has shown stability in morphological characters, herbage and oil yield. The genotype has aggressive suckers, growing under the soil surface to provide protection from adverse weather conditions and mechanical damage.

The plant is propagated vegetatively and large amount of planting materials (suckers) become available in a short period of time. This can be grown in monoculture and can be fitted into different cropping patterns in which case ploughing with disk harrow is needed to destroy the suckers and make the land suitable for the subsequent crop.

Essential oil samples were prepared from the parents as well as the hybrid of the present invention. The oil of female parent *M. arvensis* contains 80 to 82% menthol but no carvone or carvol. The pollen parent *M. spicata* contains 58% carvone in its essential oil. The Gas Liquid Chromatography (GLC) studies of these oil samples showed no peak for either menthone, menthol or menthyl acetate. But the oil samples of the hybrid contain menthol 0.66% to 2.45% and carvone 64% to 76% depending upon various states of growth. Table 2 shows important constituents of the essential oil extracted from the hybrid and analysed by GLC.

TABLE 2

| Constituents | % of total oil |
|---|---|
| 1. Limolene | 6.8–23.2 |
| 2. Menthol | 0.66–2.45 |
| 3. Carvone | 64.0–76.1 |

TABLE 3

Detailed Botantical Description:

| | |
|---|---|
| a. Stem shape: | Quadrangular |
| b. Number of nodes | |
| Main branch: | 29 +/− 4 |
| Upper branch (29th node): | 3 +/− 0 |
| Middle branch (17th node): | 6 +/− 0 |
| Lower branch (8th node): | 6 +/− 0 |
| c. Average length of internodes | |
| Main branch: (from lower to upper nodes in cm) | 1.1, 1.2, 1.3, 1.5, 1.5, 2.1, 2.2, 2.3, 2.4, 2.5, 2.6, 2.7, 2.8, 2.8, 2.8, 2.9, 2.9, 2.9, 2.8, 2.8, 2.8, 2.7, 2.7, 2.6, 2.5, 1.9, 1.1 |
| d. Leaf apex shape: | pointed (acute) |
| Leaf base shape: | pointed |
| e. Leaf shape: | Elliptical to Ovate with 4–10 finely sharp serrartions on either side. |
| f. Petiole length: | 4–6 cm |
| g. Color of upper surface of leaf: | Green group (137 A) |
| h. Color of lower surface of leaf: | Yellow green group (147 B) |
| i. Number of trichomes per leaf (Avg. Trichomes X1000): | 804 |
| j. Trichome ratio (lower leaf/upper leaf): | 215 |
| k. Time to flowering: | April–May (70 days after planting first flowering detected) |
| l. Lastingness of Bloom: | Continue till harvesting (110 days after planting) |
| m. Flower shape: | Tubular |
| n. Pedicel length: | 1–2 mm |
| o. Pedicel color: | Yellow green group (146 C) |
| p. Calyx diameter: | 1 mm, four fused |
| q. Calyx color: | Yellow green group (146 C) |
| r. Corolla: | Four, fused to a corolla tube |
| s. Corolla color: | Purple group (76 D) |
| t. Pubescence of corolla: | smooth |
| u. Number of anthers: | Four, ocididimetry, remain inside the corolla tube |
| v. Color Designation: | Red purple group (59 A) |
| w. Stigma: | bifid |
| x. Ovaries: | Bicarpellary, syncarpous |
| y. Color of stigma: | Violet group (85 C) |
| z. Color of ovaries: | Yellow green group (151 A) |

The above examples are only illustrative in nature and should not be construed to limit the scope of the invention.

Statement of Distinction

As evident from morphology, the hybrid is distinct from the parents *Mentha arvensis* (cv Kalka) and *Mentha spicata* (cv Neera) and the natural species *Mentha cardiaca*.

The essential oil of the hybrid contains menthol and carvone where as those of the parents contain either menthol or carvone.

The hybrid is superior in growth habit in comparison to natural species *M. cardiaca*. The hybrid also has a higher biomass and oil yield.

The essential oil of the hybrid has predominantly a carvone smell with menthol tinge which is special and unique.

RAPD profile analysis shows codominant polymorphic bands in the hybrid from Kalka and Neera when the genomic DNA is amplified with primer MAP 03 .

The hybrid contains 2n=72 chromosomes in comparison to the parents *Mentha arvensis* (cv Kalka) 2n=96 and *Mentha spicata* (cv Neera) 2n—48.

Randomly Amplified Polymorphic DNA Analysis

The RAPD patterns of the hybrid are completely different from those of the parents as well as the *M. cardiaca* which is thought to be the natural hybrid of *M. arvesnsis* and *M. spicata*. The hybrid of the present invention was developed by crossing *M. arvensis* (cv Kalka) and *M. spicata* (cv Neera) and is thus unique and novel. The following primers were used to develop a unique and distinct RAPD profile of the hybrid (Table 4).

TABLE 4

| Primers | Nucleotide Sequence |
|---|---|
| 1.MAP 01 | 5'AAA TCG GAG C3' |
| 2.MAP 02 | 5'GTC CTA CTC GC3' |
| 3.MAP 03 | 5'GTC CTT AGC G3' |
| 4.MAP 04 | 5'TGC GCG ATC G3' |
| 5.MAP 05 | 5'AAC GTA CGC G3' |
| 6.MAP 06 | 5'GCA CGC CGG A3' |
| 7.MAP 07 | 5'CAC CCT GCG C3' |
| 8.MAP 08 | 5'CTA TCG CCG C3' |
| 9.MAP 09 | 5'CGG GAT CCG C3' |
| 10.MAP 10 | 5'GCG AAT TCC G3' |
| 11.MAP 11 | 5'CCC TGC AGG C3' |
| 12.MAP 12 | 5'CCA AGC TTG C3' |

MAP—Medicinal and Aromatic Plants

The co-dominance of the Polymerase Chain Reaction (PCR) amplified bands with printer MAP 03 in the hybrid from *M. arvensis* (Kalka) and *M. spicata* (Neera) is clear. So the hybrid of the present invention is distinct, unique, novel and can be used for different medicinal and aromatic purposes. The hybrid has better morphological and economical traits and at present is available only with CIMAP.

In addition to the characteristics features described in table 1, the novel hybrid has the following features:

(a) No. of leaves at each node=2.

(b) No. of leaves at the apex=4.

(c) Phyllotaxy: Opposite deccusate (d) Fertilizer dose (Kg/ha): 150:30:30 (N:P:K)—Urea, SSP, MOP (e) Maturity:110 days ('Neerkalka' & *M. spicata* pollen parent, 120 days Mother parent: M. arvensis)

(f) Oil odour: 'Neerkalka': Carvone based with menthol tinge, 'Kalka': Menthol based and 'Neera'; Carvone based.

(g) Stem thickness: 4–5 mm (at $5^{th}$ internode, standard method)

(h) Agroclimatic conditions: Temp. 18–37° C. (Maximum,) 8–22° C. (Minimum).

We claim:

1. A new and distinct variety of interspecific mint plant, as herein described and illustrated.

* * * * *